(12) United States Patent
Akdag

(10) Patent No.: US 11,871,912 B2
(45) Date of Patent: Jan. 16, 2024

(54) ARTHROSCOPIC TOOL ATTACHMENT WITH OBJECT SEPARATOR

(71) Applicant: Vedat Akdag, Ventura, CA (US)

(72) Inventor: Vedat Akdag, Ventura, CA (US)

( * ) Notice: Subject to any disclaimer, the term of this patent is extended or adjusted under 35 U.S.C. 154(b) by 367 days.

(21) Appl. No.: 17/346,262

(22) Filed: Jun. 13, 2021

(65) Prior Publication Data
US 2022/0395172 A1    Dec. 15, 2022
US 2023/0371806 A9    Nov. 23, 2023

Related U.S. Application Data

(60) Provisional application No. 63/048,075, filed on Jul. 3, 2020.

(51) Int. Cl.
*A61B 1/32* (2006.01)
*A61B 1/00* (2006.01)
*A61B 1/317* (2006.01)

(52) U.S. Cl.
CPC ............ *A61B 1/32* (2013.01); *A61B 1/00128* (2013.01); *A61B 1/00133* (2013.01); *A61B 1/317* (2013.01)

(58) Field of Classification Search
CPC ....... A61B 1/32; A61B 1/00133; A61B 1/317; A61B 17/16
USPC ................................................... 600/184–245
See application file for complete search history.

(56) References Cited

U.S. PATENT DOCUMENTS

2005/0256368 A1* 11/2005 Klenk .................... A61F 2/2481
  606/108
2006/0129026 A1* 6/2006 Wallin ................... B29C 70/766
  264/299

* cited by examiner

*Primary Examiner* — Eduardo C Robert
*Assistant Examiner* — Tara Rose E Carter
(74) *Attorney, Agent, or Firm* — Metropolis IP Group, LLC; Eric Kang

(57) ABSTRACT

An attachment apparatus to an arthroscopic tool, comprising at one axial distal end of the attachment, a pushrod end collar of tubular cross section with a hook or fastening provision at one axial distal end of said pushrod end collar to connect to a force applicator and, rigidly attached at the other axial distal end of the pushrod end collar, are at least two pairs of pushrods, wherein each pair of said pushrods are tangentially situated at opposite ends of the pushrod end collar and extends away from the pushrod end collar into channels or grooves of a pushrod guide sleeve with tubular cross section, wherein one distal end of the pushrod guide sleeve is at least a pair of cutouts for a plurality of lifting tabs placed at opposite radial distal ends along the circumference of the pushrod guide sleeve.

7 Claims, 7 Drawing Sheets

ARTHROSCOPIC TOOL ATTACHMENT WITH OBJECT SEPARATOR

CROSS-REFERENCE TO RELATED APPLICATIONS

The present application claims priority to provisional patent application number 63/048,075 filed on Jul. 3, 2020, disclosures of which are incorporated herein at least by reference.

BACKGROUND OF THE INVENTION

1. Field of the Invention

The invention relates apparatuses for arthroscopic procedures and methods for use.

2. Discussion of the State of the Art

Many surgical procedures require guidance from optical tools such as cameras or scopes. There are many situations where optical functionality is not possible due to non-transparent objects or organic matter like bone(s) or tissue in the line-of-sight (LOS) occluding the region of interest. If the organic matter is a bone, the current workaround may be to first drill a hole through the bone and pass the camera or scope through. Aside from reducing the bone's load bearing capacity and fatigue life, these extra steps add extra time, cost, and risk of complications in the overall procedure. A solution to these problems is a novel arthroscopic tool attachment with an object separator that is disclosed in the following sections.

SUMMARY OF THE INVENTION

The present disclosure focuses on an annular attachment to an arthroscopic tool that separates adjoining non-transparent objects or organic matter such as bones and/or soft matter. This apparatus separates objects by way of lifting tabs that extend radially outward. The lifting tabs in turn are attached to a set of sliding arms, herein called pushrods, arranged substantially parallel and just external to the barrel of the arthroscopic tool. The opposite end of the pushrods is attached to a pushrod end collar. The pushrod end collar and pushrods are able to move together relative to the arthroscopic tool and pushrod guide sleeve when sufficient translational or linear force is applied to the pushrod end collar in the direction toward the optical sensing end or lens opening of the arthroscopic tool. The pushrod guide sleeve kinematically guides the pushrods and is separated from the pushrod end collar by a distance greater than the length the lifting tabs fully deploy from its seated position in the pushrod guide sleeve.

A linear force applied to the pushrod end collar can be achieved by a range of means. The embodiment disclosed here to achieve linear force application is an apparatus that bears some resemblance to a caulking gun, herein called a linear force driver. After the linear force driver is coupled to the arthroscopic tool, a translational force directed to the pushrod end collar can be applied by squeezing the two linear force driver handles. Sufficient translational force will displace the pushrod end collar, which in turn pushes the pushrods to raise the lifting tabs radially away from its seated position to separate adjoining organic matter. The lifting tabs can be made to rotate about the closest edge of the pushros arm pivot so that the surface of the lifting tabs conforms as close as possible to the angle of the engaged surface.

BRIEF DESCRIPTION OF THE DRAWING FIGURES

The drawings are provided to facilitate understanding in the detailed description. It should be noted that the drawing figures may be in simplified form and might not be to precise scale. In reference to the disclosure herein, for purposes of convenience and clarity only, directional terms such as top, bottom, left, right, up, down, over, above, below, beneath, rear, front, distal, and proximal are used with respect to the accompanying drawings. Such directional terms should not be construed to limit the scope of the embodiment in any manner.

Figure 3:
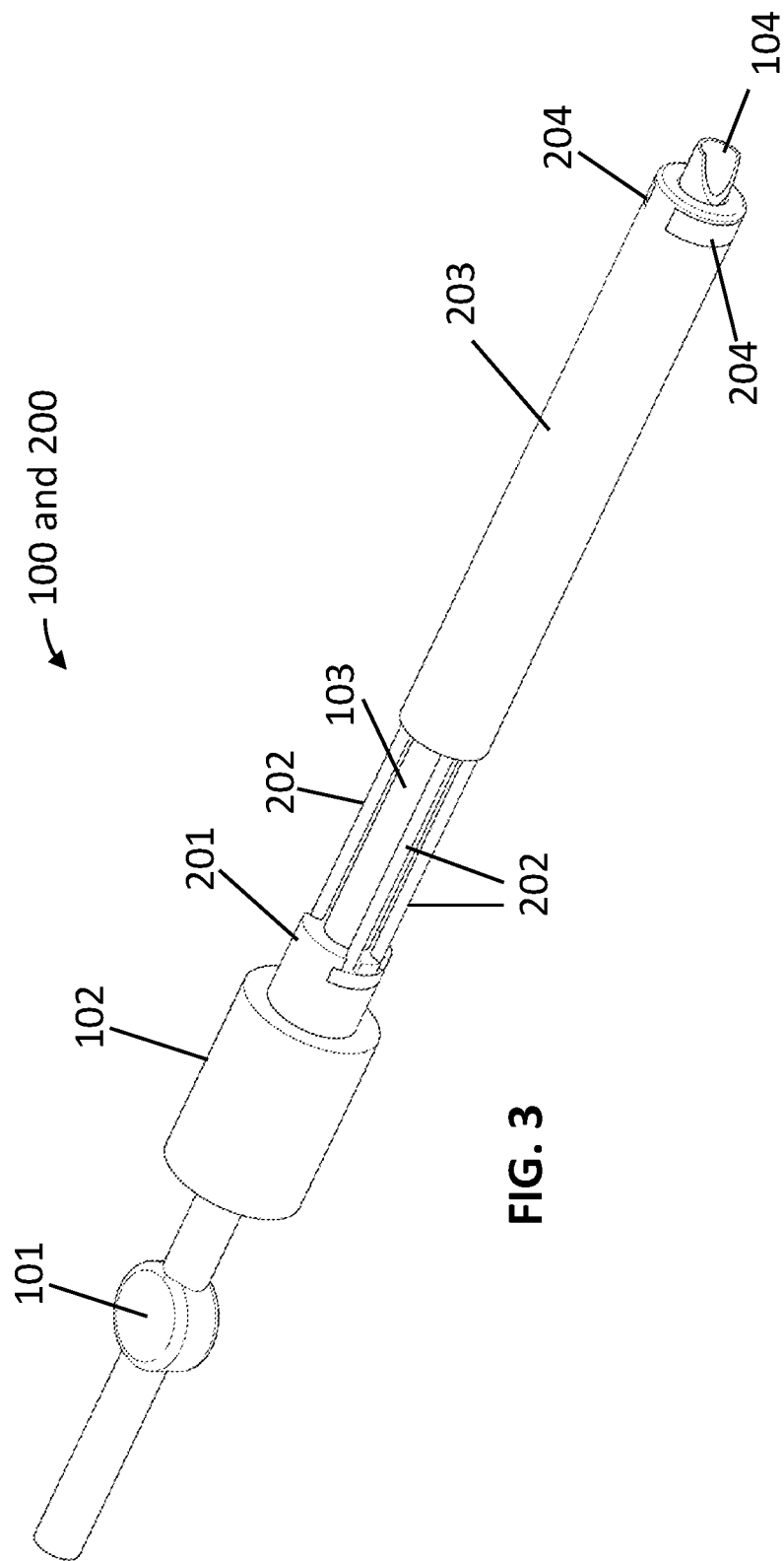
Figure 4:
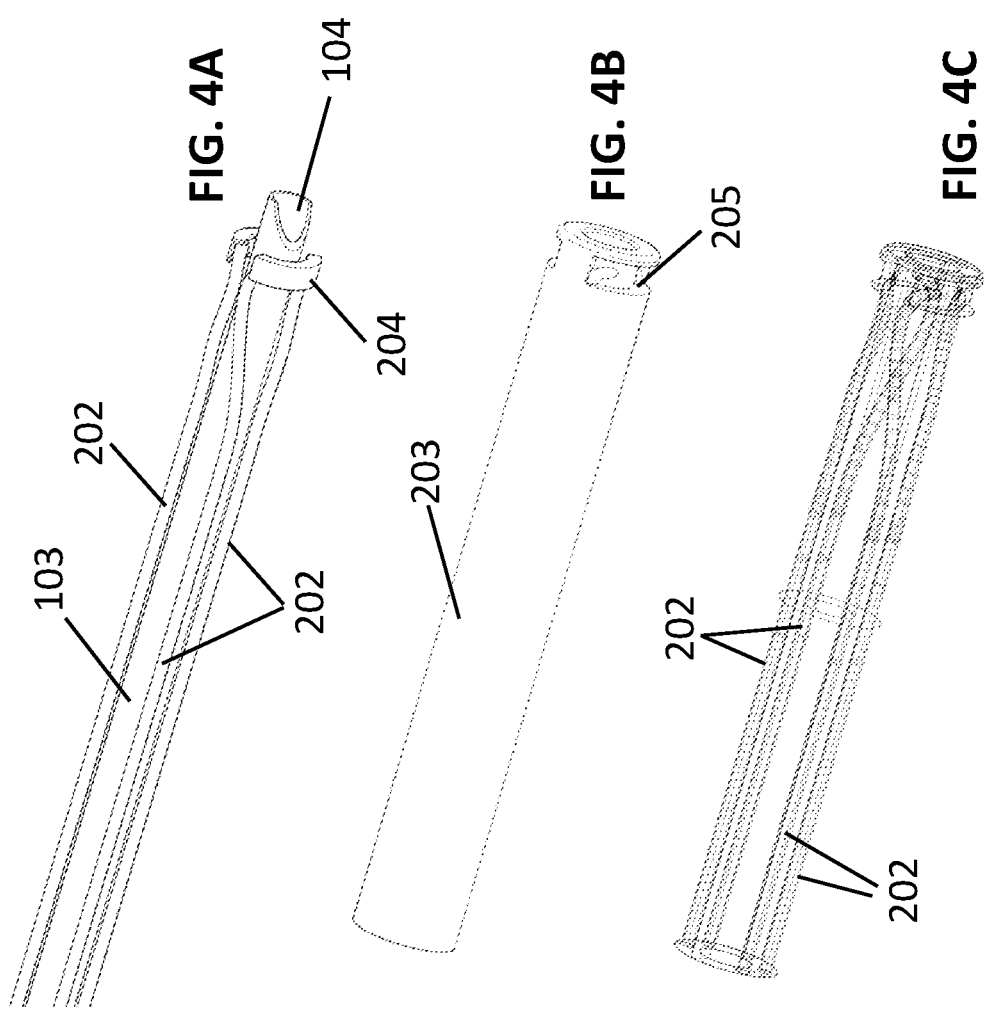
Figure 5:
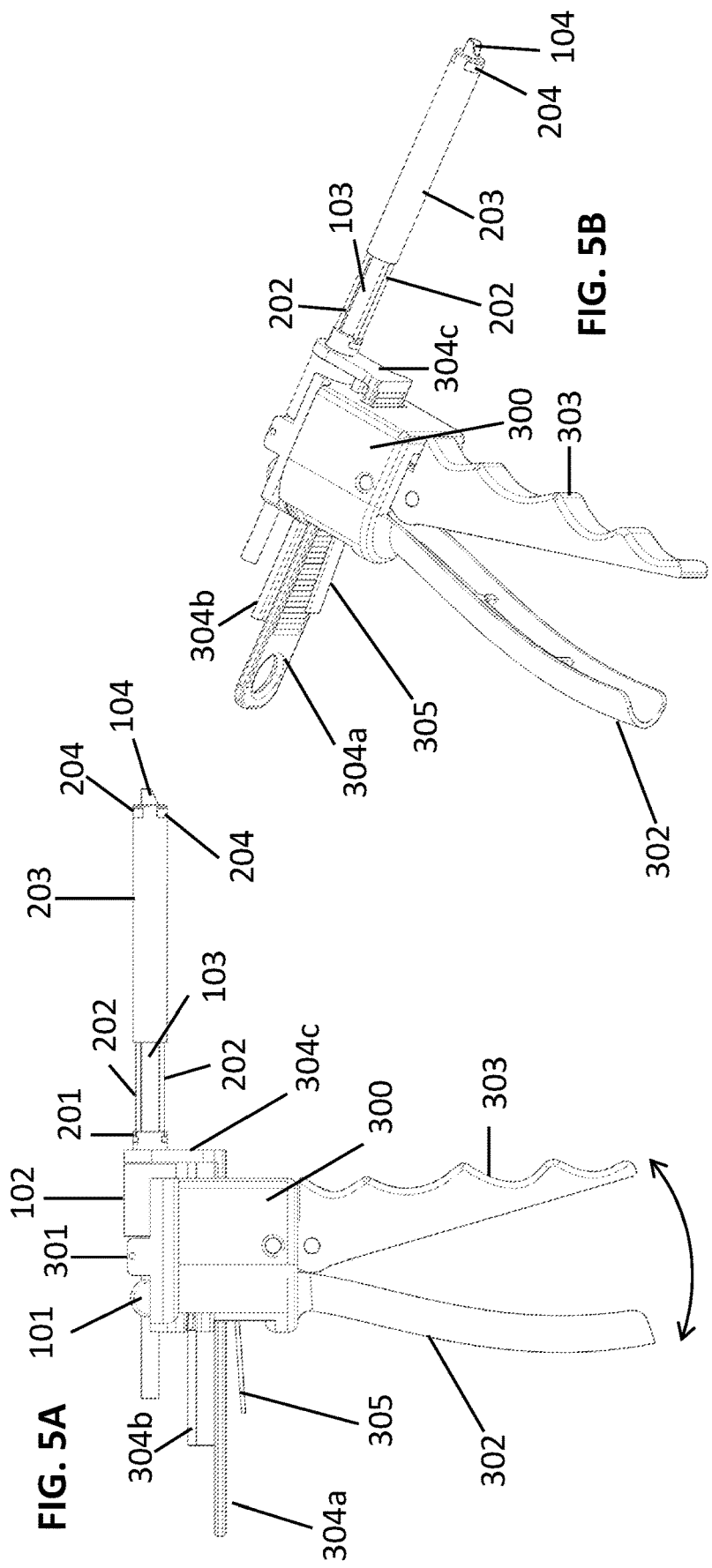
Figure 6:
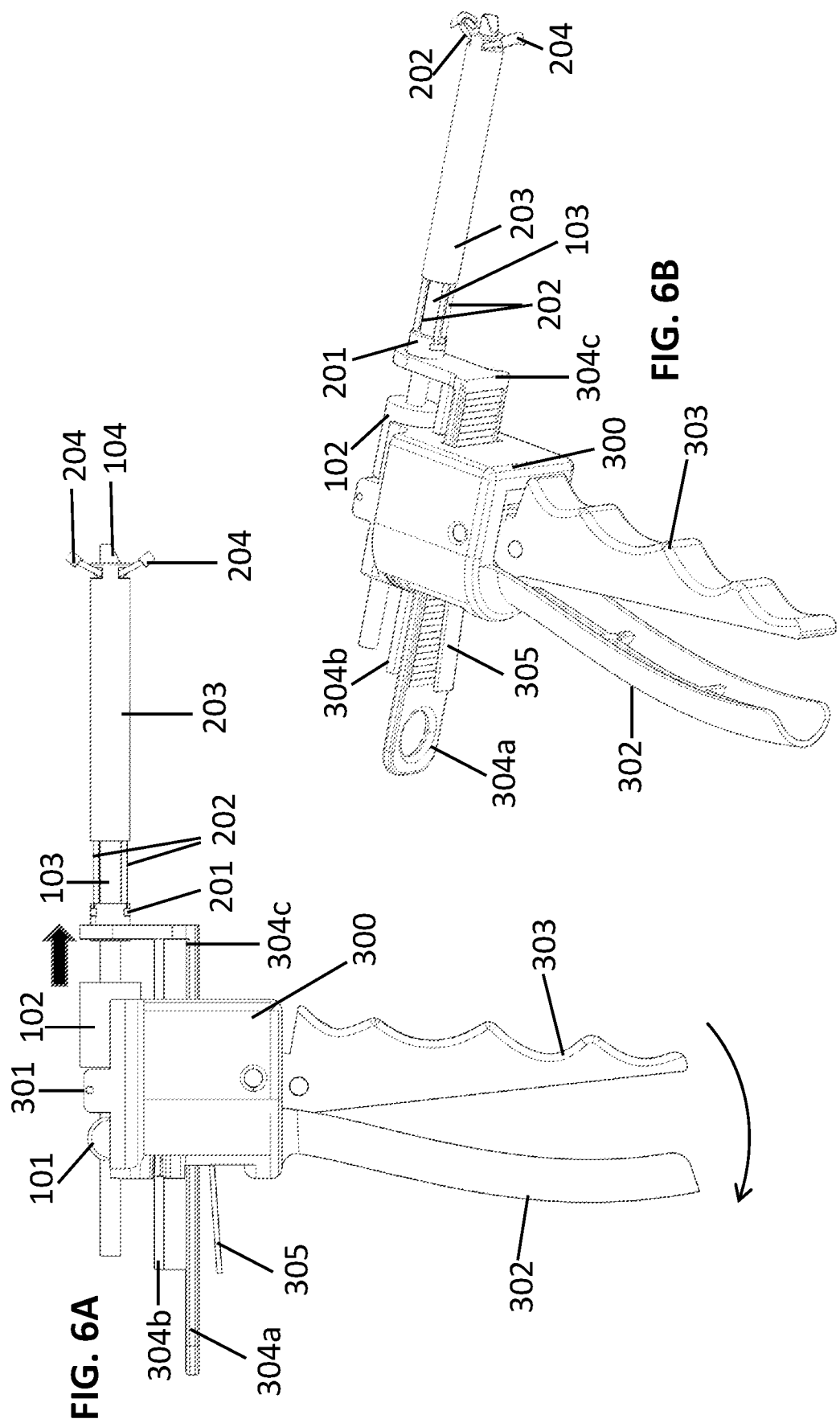
Figure 7:
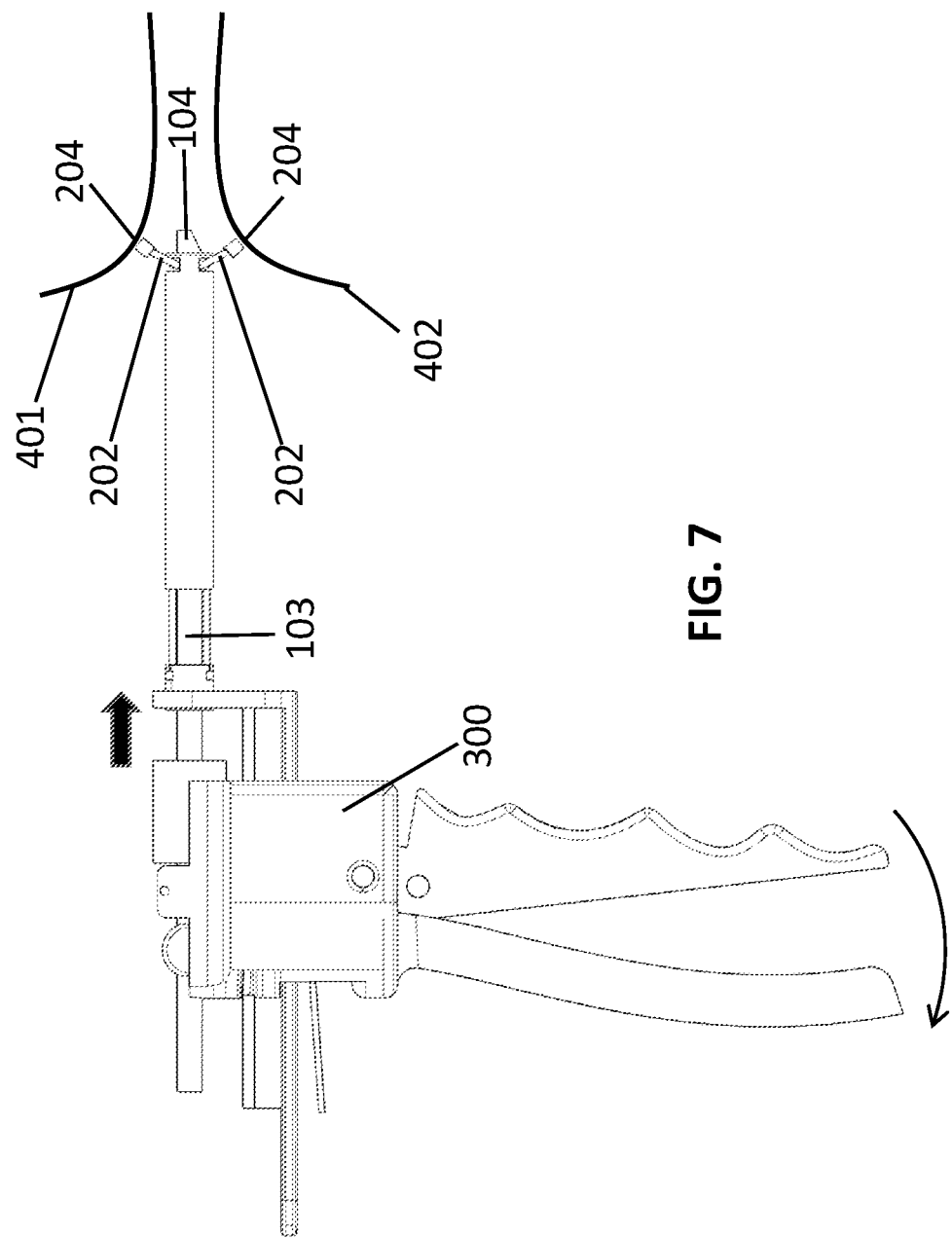

FIG. 3 is a tilted view of the object separator attached to the arthroscopic tool FIG. 4A shows a tilted view of the lens opening of the arthroscopic tool's hollow tube surrounded by pushrods and lifting tabs of the attachment FIG. 4B is a tilted view of the pushrod guide sleeve and tab opening for the pushrods and lifting tabs FIG. 4C is a wireframe view of the combined assembly shown in FIGS. 4A and 4B FIGS. 5A and 5B show profile and tilted views of an exemplary linear force driver attached to the attachment and arthroscopic tool, respectively FIGS. 6A and 6B show profile and tilted views of the exemplary linear force driver attached to the attachment and arthroscopic tool, respectively, with the lifting tabs deployed FIG. 7 is a profile view of the exemplary linear force driver attached to the attachment and arthroscopic tool with the lifting tabs deployed to separate organic matter

DETAILED DESCRIPTION

Figure 1:
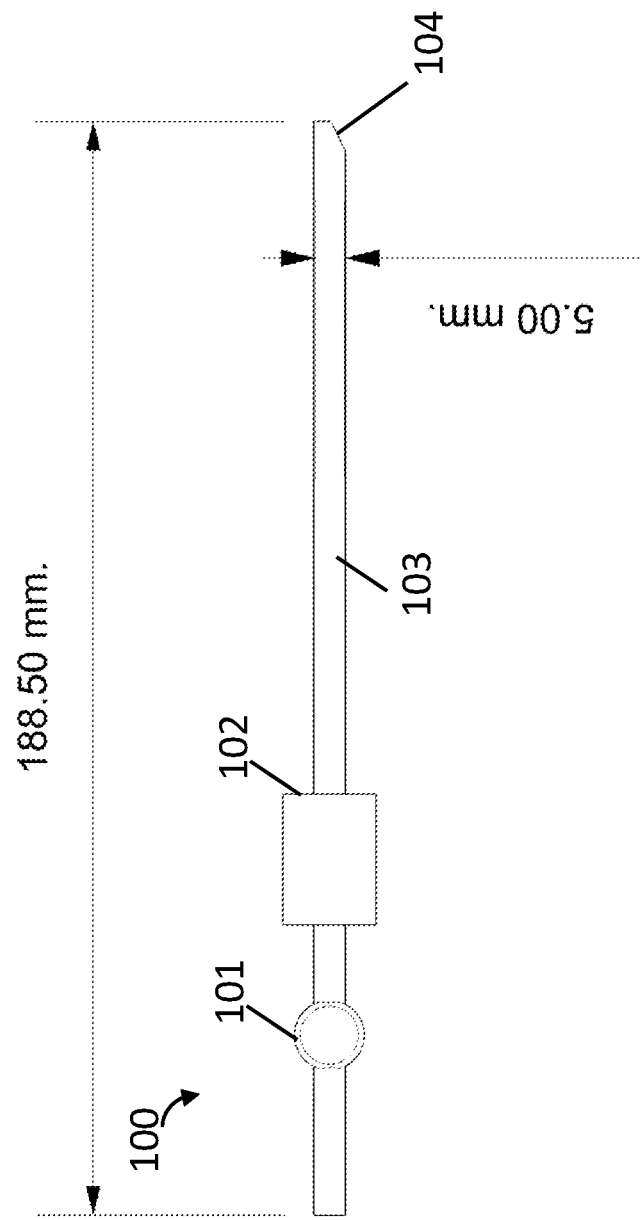
FIG. 1 is a profile view of an exemplary arthroscopic tool

FIG. 1 shows an exemplary arthroscopic tool (100) with a tab (101) and tool collar (102) that are both fixed to the hollow tool tube (103) running the substantial length of the arthroscopic tool (100). The tab (101) and tool collar (102) may be separated by a finite distance as shown. One end of the tool tube (103) has a camera or scope lens opening (104). This lens opening (104) may have an angled cut as shown. Oftentimes in surgical procedures, this lens opening (104) faces a non-transparent obstacle occluding the region of interest. If the obstacles are adjoining but can be separated to some degree, such as two bones forming a joint, then the disclosed object separator attachment apparatus, herein termed "attachment" (200), can separate the adjoining objects to enable optical access to the area of interest. The dimensions shown only reflect the exemplary arthroscopic tool (100) and are not meant to limit the range of applicability as embodiments of the disclosed invention are invariant to any specific scale or proportions.

Figure 2:
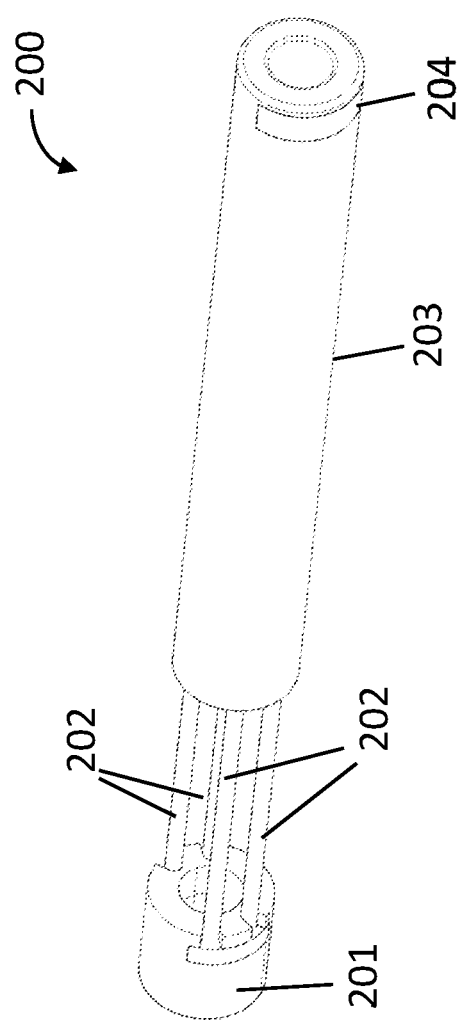
FIG. 2 is the tilted view of an object separator attachment

FIG. 2 shows a tilted view of an embodiment of the attachment (200). On one distal end of the attachment (200) is a pushrod end collar (201) with a tubular cross section. Rigidly fixed at one distal end of the slide end collar (201) and at its radial distal extent are at least two pairs of pushrods (202). The embodiment shown depicts four pushrods (202), where each pair of closely located pushrods (202) are tangentially situated at opposite ends of the pushrod end collar (201), extends away from the pushrod end collar (201), and into channels or grooves (not shown) of a pushrod guide sleeve (203). The pushrods (202) move relative to the pushrod guide sleeve (203). At one distal end of the pushrod guide sleeve (203) is at least a pair of cutouts for a plurality of lifting tabs (204) placed at opposite radial distal ends along the curved outer surface of the pushrod guide sleeve (203). The pushrod guide sleeve (203) has a tubular cross-section.

FIG. 3 shows the attachment (200) coupled to the arthroscopic tool (100), which is accomplished by sliding the tool tube (103) through the bore of the pushrod end collar (201), in between the pushrods (202), and through the bore of the pushrod guide sleeve (203). One geometric requirement is the combination of the axial dimension of the pushrod end collar (201), axial distance of an intermediate external element capable of imparting force to said pushrod end collar (304c from FIGS. 5A, 5B, 6A, and 6B), axial distance between the pushrod end collar (201) and pushrod guide sleeve (203), and axial dimension of the pushrod guide sleeve (203) is such that the pushrod guide sleeve (203) does not extend over or past the lens opening (104). The second geometric requirement is the axial distance between the pushrod end collar (201) and pushrod guide sleeve (203) is larger than the axial displacement of the pushrod end collar (201) needed to fully deploy the lifting tabs (204). While the pushrod end collar (201) and pushrod (202) are free to translate relative to the tool tube (103) during deployment and retraction of the lifting tabs (204), the pushrod guide sleeve (203) remains fixed to the tool tube (103). The pushrod guide sleeve (203) can be fixed to the tool tube (103) by a range of embodiments. An exemplary embodiment not depicted in any of the figures is to have one countersunk setscrew fastened through a corresponding tap placed on at least one of the two axial extents of the pushrod guide sleeve (203), approximately 90 degrees offset from the space between one of the pairs of pushrods (202). When the setscrew is applying preload, the tip of each setscrew is pressed onto the tool tube (103) to generate sufficient friction or restraining force to keep the pushrod guide sleeve (203) fixed to the tool tube (103) during operation. While FIG. 3 shows the pushrod end collar (201) engaging the tool collar (102), actually during operation, as will be shown in FIGS. 5A, 5B, 6A, 6B, and 7, said external element (304c) is placed between the tool collar (102) and pushrod end collar (201) and should be in constant contact with the pushrod end collar (201) when imparting a translating force to the pushrod end collar (201).

FIG. 4A illustrates the pushrods (202) in proximity and substantially parallel to the outer surface of the tool tube (103). At the distal axial end of the pushrods (202) near the lens opening (104), are lifting tabs (204), which for the embodiment shown, each tab having a cupped profile that conforms tangentially to the round outer surface of the tool tube (103) and is flush with the round outer surface of the pushrod guide sleeve (203) when the lifting tabs (204) are fully seated in said tab opening (205). The embodiment depicted in this disclosure has one lifting tab (204) attached to one pair of pushrods (202) on each side of the tool tube (103). The lifting tabs (204) can be rigidly fixed to the pushrods (202). However, other embodiments can have the lifting tabs (204) constructed to pivot relative to the edge of the pushrods (202) so that the lifting tabs (204) can conform to the angle of engagement with the interfacing object to be displaced. One example would have each of the lifting tabs (204) be pinned to an edge of each pushrod (202), where a pin runs along the edge of each pushrod (202).

FIG. 4B shows a tilted view of the pushrod guide sleeve (203) and tab opening (205) for the pushrod (202) and lifting tabs (204) to pass through. As previously mentioned, in its fully seated position, the lifting tabs (204) sit in the tab opening (205) such that the convex side of the lifting tabs (204) conforms to the outer surface contour of the pushrod guide sleeve (203) in a same manner a puzzle piece completes a puzzle.

FIG. 4C shows a wireframe view of the combined assembly of FIGS. 4A and 4B so that the relational form between the pushrod (202), pushrod guide sleeve (203), lifting tabs (204), and tab opening (205) in the fully seated position of the lifting tabs (204) is apparent.

Embodiments of a separate device to apply translational force to the pushrod end collar (201) and displace the pushrods (202) and the lifting tabs (204) can vary and include one or more of the following: a linear stepper motor, a force transducer, return spring mechanism, or a hand squeeze trigger-style ratchet and release mechanism embodiment shown in FIGS. 5A, 5B, 6A, 6B, and 7. FIGS. 5A and 5B show profile and tilted views of the hand squeeze trigger-style ratchet and release mechanism embodiment (300) attached to the attachment (200) and arthroscopic tool (100), respectively. A ridge (301) molded with the main chassis of the linear force driver (300) is shown to fit snugly between the tab (101) and tool collar (102). A fixed handle (302) and trigger (303) is shown to branch off the internal mechanism (not shown) of the linear force driver (300). The pushrod tracks (304a and 304b) and force applicator (304c) are one integrated part. One embodiment of the lower pushrod track (304a) has a grooved surface topology so a rachet mechanism and associated gear can lock onto the pushrod track and enforce single direction movement while the trigger (303) is squeezed toward the fixed handle (302) to deploy the lifting tabs (204). Each successive squeeze and release of the trigger (303) moves the force applicator (304c), pushrod end collar (201), and pushrods (202) in one direction so that the lifting tabs (204) lift off or further away from its seated position until the lifting tabs (204) are fully deployed. When the ratchet release (305) is deflected by the user toward the lower pushrod track (304a), the single direction lock (not shown) is released and the lower pushrod track (304a) along with the train of components including the pushrod end collar (201), pushrods (202), and lifting tabs (204) can be retracted. A restoring force achieved by a spring (not shown) can be implemented to ensure the lifting tabs (204) can fully retract to their seated position when the ratchet is unlocked. This, in turn, would require the force applicator (304c) to "hook into" the pushrod end collar (201) so the force applicator (304c) can also pull the pushrod end collar (201) to retract the lifting tabs (204).

FIGS. 6A and 6B show profile and tilted views of the linear force driver attached to the attachment (200) and arthroscopic tool (100), respectively, with the lifting tabs (204) deployed. Compared to FIGS. 5A and 5B, one can clearly see from FIGS. 6A, 6B, and 7 the force applicator (304c) translating away from the tool collar (102) and translating the pushrod end collar (201) such that the pushrods (202) move further into the pushrod guide sleeve (203). The channels (not shown) along the bore surface of the pushrod guide sleeve (203), kinematically guide the pushrods (202) such that the lifting tabs (204) project radially outward as shown.

FIG. 7 is based on FIG. 6A with an added depiction of the initially adjoining objects (401 and 402) being separated. As a non-limiting, illustrative example, the objects (401 and 402) can be a femur and tibia bone. It is readily apparent that the scope lens near the lens opening (104) now has LOS optical access past the objects (401 and 402) to the region of interest.

The preferred embodiment of materials for all components of the attachment (200) should be biocompatible. Hence, the preferred embodiment of the components (201-205) should not adversely interact with surrounding organic matter nor be toxic to the patient nor degrade when inside the medical patient. The preferred properties embodiment of the pushrod end collar (201), pushrod guide sleeve (203), and lifting tabs (204) should be hard and resist deflection under normal loads yet also not be brittle. The preferred embodiment of the channels (not shown) in the pushrod guide sleeve (203) may have a low friction, non-toxic coating to minimize both friction and the adverse chance for the pushrods (202) to bind. The pushrods (202) themselves along at least the portion that can slide along the channels of the pushrod guide sleeve (203) may also have a low friction coating.

The pushrods (202) are structurally designed to resist buckling within the distance between the pushrod end collar (201) and pushrod guide sleeve (203) while the lifting tabs (204) apply the necessary force to separate objects (401 and 402). However, the enabling embodiments of the pushrods (202) are not limited to one combination of the cross-sectional design, cross-sectional area moment of inertia, and material selection. At the same time, the pushrods (202) near the lifting tabs (204) need to be flexible enough to slide along the channels in the pushrod guide sleeve (203) that are curved so that the lifting tabs (204) deploy radially outward from the pushrod guide sleeve (203) to create sufficient clearance between the objects (401 and 402). Hence, the pushrods (202) may be designed to have varying levels of modulus of elasticity along its entire length. Alternatively, a single material and cross-section pushrod dimension may be used if sufficiently rigid in buckling and sufficiently flexible in bending when lifting the end tabs (204).

Many alterations and modifications may be made by those having ordinary skill in the art without departing from the spirit and scope of the embodiment. Therefore, it must be understood that the illustrated embodiment has been set forth only for the purposes of example and that it should not be taken as limiting the embodiment.

The words used in this specification to describe the embodiment and its various embodiments are to be understood not only in the sense of their commonly defined meanings but to include by special definition in this specification structure, material, or acts beyond the scope of the commonly defined meanings.

What is claimed is:

1. An attachment apparatus to an arthroscopic tool, comprising:
    at one axial distal end of the attachment, a pushrod end collar of tubular cross-section engageable to an external element capable of imparting force to said pushrod end collar and rigidly attached to the other axial distal end of the pushrod end collar, are at least two pairs of pushrods;
    wherein each pair of said pushrods are tangentially situated at opposite ends of the pushrod end collar and extends away from the pushrod end collar into channels or grooves of a pushrod guide sleeve with tubular cross-section;
    wherein one distal end of the pushrod guide sleeve is at least a pair of cutouts for a plurality of lifting tabs placed at opposite ends of the curved outer surface of said pushrod guide sleeve;
    said cutouts are axially located near the end of said pushrod guide sleeve furthest from said pushrod end collar;
    wherein each of said lifting tabs is attached to a pushrod on the end that is opposite from the pushrod end collar;
    wherein said channels along the bore surface of the pushrod guide sleeve kinematically guide the pushrods such that the lifting tabs project radially outward from the axis and curved outer surface of the pushrod guide sleeve when deployed.

2. The attachment apparatus to an arthroscopic tool according to claim 1, wherein each lifting tab has a cupped profile whose inner surface is concave and whose curve outer surface is convex such that the outer surface of said tab is flush to the curved outer surface of the pushrod guide sleeve when the lifting tabs are fully seated or retracted in said cutout.

3. A system including the apparatus to an arthroscopic tool recited in claim 1:
    wherein said attachment is attached to an arthroscopic tool;
    said arthroscopic tool having a long slender hollow tube;
    said tool tube disposed through a tab near the opposite end of the tool tube opening where a camera or scope lens is situated;
    said tool tube disposed through a tool collar that is offset from the center but with a finite distance from said tab;
    said attachment coupled to said arthroscopic tool after sliding said tool tube through the bore of the pushrod end collar, in between the pushrods and through the bore of the pushrod guide sleeve;
    wherein the combined axial dimension of the pushrod end collar, axial distance of said external element, axial distance between the pushrod end collar and pushrod guide sleeve, and axial dimension of the pushrod guide sleeve is such that the pushrod guide sleeve does not extend over or past the lens opening;
    and the axial distance between the pushrod end collar and pushrod guide sleeve is larger than the axial displacement of the pushrod end collar needed to fully deploy the lifting tabs;
    and a linear force driver, which can be any one or more of the following mechanisms comprising a linear stepper motor, a force transducer, a return spring mechanism, or a hand squeeze trigger-style ratchet and release mechanism.

4. The system according to claim 3:
    wherein said pushrod guide sleeve is fixed to the tool tube by one countersunk setscrew fastened through a corresponding tap placed on at least one of the two axial distal ends of the pushrod guide sleeve and is approximately 90 degrees offset from the space between one of the pairs of pushrods such that when the setscrew is applying preload, the tip of each setscrew is pressing onto the tool tube to generate sufficient friction or restraining force to keep the pushrod guide sleeve fixed to the tool tube during operation;
    said linear force driver is axially constrained by the use of a structural element shaped to fit around a hollow tube that defines much of the axial portion of the arthroscopic tool's structure and be axially in between a tab and tool collar that are both fixed to said tool tube but separated by a finite distance.

5. A method of deploying or retracting a plurality of lifting tabs of an attachment apparatus to an arthroscopic tool as recited in claim 1, whereby:

the deployment or retracting of said lifting tabs is the result of a linear force provided by a linear force driver, which can be any one or more of the following mechanisms comprising a linear stepper motor, a force transducer, return spring mechanism, or a hand squeeze trigger-style ratchet and release mechanism;

wherein said linear force is transferred from said external element to said pushrod end collar to linearly displace a train of components comprising said pushrod end collar, said pushrods, and said lifting tabs attached to one of the distal ends of the pushrods, wherein said linear force driver is axially constrained by the use of a structural element shaped to fit around a hollow tube that defines much of the axial portion of the arthroscopic tool's structure and be axially in between a tab and tool collar that are both fixed to said tool tube but separated by a finite distance.

6. The method of claim 5, further comprising:

deploying said lifting tabs by squeezing a trigger of a trigger-style ratchet and release mechanism;

wherein each successive squeeze and release of said trigger moves a pushrod track with a grooved surface topology so an internal rachet mechanism and associated gear can lock onto the pushrod track and enforce single direction movement of the force applicator that is integrated with said pushrod track and so that said train of components is displaced in a direction such that said lifting tabs lift off or moves further away from its seated position.

7. The method of claim 6, further comprising:

retracting said lifting tabs by actuating a ratchet release to allow an internal rachet mechanism and gear engaging a pushrod track integrated with said force applicator to release its uni-directional lock, thereby allowing the force of an initially stretched or compressed return spring mechanism to displace said pushrod track, force applicator, and train of components in a direction that retracts the lifting tabs toward its seated position.

* * * * *